(12) United States Patent
Payne et al.

(10) Patent No.: US 7,438,411 B2
(45) Date of Patent: Oct. 21, 2008

(54) PLASMON RESONANT BASED EYE PROTECTION

(75) Inventors: J. Donald Payne, Kingwood, TX (US); Joseph B. Jackson, Houston, TX (US)

(73) Assignee: Nanospectra Biosciences, Inc., Houston, TX (US)

( * ) Notice: Subject to any disclaimer, the term of this patent is extended or adjusted under 35 U.S.C. 154(b) by 38 days.

(21) Appl. No.: 11/418,893

(22) Filed: May 5, 2006

(65) Prior Publication Data

US 2006/0275596 A1 Dec. 7, 2006

Related U.S. Application Data

(60) Provisional application No. 60/678,754, filed on May 7, 2005.

(51) Int. Cl.
*G02C 7/10* (2006.01)
(52) U.S. Cl. .................. 351/159; 351/160 R; 351/163; 351/177
(58) Field of Classification Search ......... 351/159–177; 359/159–177
See application file for complete search history.

(56) References Cited

U.S. PATENT DOCUMENTS

| | | | |
|---|---|---|---|
| 4,084,458 A * | 4/1978 | Galley ........................ 82/1.11 |
| 4,229,273 A | 10/1980 | Wajs | |
| 4,338,822 A | 7/1982 | Yamaguchi et al. | |
| 4,669,834 A | 6/1987 | Richter | |
| 4,816,145 A | 3/1989 | Goudy, Jr. | |
| 4,837,289 A | 6/1989 | Mueller et al. | |
| 4,841,149 A | 6/1989 | Martin et al. | |
| 4,896,958 A | 1/1990 | Ames et al. | |
| 4,990,582 A | 2/1991 | Salamone | |
| 5,043,004 A | 8/1991 | Miyauchi | |
| 5,106,930 A | 4/1992 | Gupta | |
| 5,137,767 A | 8/1992 | Miyauchi et al. | |
| 5,159,486 A | 10/1992 | Webb | |
| 5,208,648 A | 5/1993 | Batchelder et al. | |
| 5,220,403 A | 6/1993 | Batchelder et al. | |
| 5,480,927 A | 1/1996 | Janssen et al. | |
| 5,681,871 A | 10/1997 | Molock et al. | |
| 5,684,059 A | 11/1997 | Salamone | |
| 5,693,095 A | 12/1997 | Freeman et al. | |
| 5,717,203 A | 2/1998 | Yung | |
| 5,770,125 A | 6/1998 | O'Connor et al. | |
| 5,770,637 A | 6/1998 | Vanderlaan et al. | |
| 5,804,107 A | 9/1998 | Martin et al. | |

(Continued)

*Primary Examiner*—Darryl J Collins
(74) *Attorney, Agent, or Firm*—Jackson Walker L.L.P.; Mark Tidwell, Esq.

(57) ABSTRACT

A contact lens is provided in which tunable nanoparticles are embedded or otherwise coated on the lens to extinguish near-infrared energy. In one preferred embodiment, the tunable nanoparticles are nanoshells consisting of a dielectric core and a metal shell, wherein the plasmon resonance frequency is determined by the relative size of the core and the metal shell. With the capability to alter the relative size of the core and the metal shell, nanoshells are uniquely tunable nanoparticles, allowing a range of optical extinctions. In another embodiment, the nanoshells are tuned to extinguish energy from other parts of the energy spectrum. In one desired embodiment of the invention, these plasmon resonant structures are introduced into the lens polymer prior to formation or manufacturing of a lens. In another embodiment of the invention, these nanoshells are coated on a contact lens after formation of the lens.

66 Claims, 9 Drawing Sheets

U.S. PATENT DOCUMENTS

| | | | |
|---|---|---|---|
| 5,981,617 | A | 11/1999 | Kim et al. |
| 5,997,472 | A | 12/1999 | Bonnell et al. |
| 6,012,814 | A | 1/2000 | Wood |
| 6,118,913 | A | 9/2000 | O'Connor et al. |
| 6,124,594 | A | 9/2000 | Duggan et al. |
| 6,183,083 | B1 | 2/2001 | Ocampo |
| 6,239,433 | B1 | 5/2001 | Porter |
| 6,294,786 | B1 | 9/2001 | Marcichow et al. |
| 6,312,127 | B1 | 11/2001 | Ocampo |
| 6,344,272 | B1 | 2/2002 | Oldenburg et al. |
| 6,347,242 | B1 | 2/2002 | Friedlander |
| 6,428,811 | B1 | 8/2002 | West et al. |
| 6,471,396 | B2 | 10/2002 | Biel |
| 6,511,617 | B1 | 1/2003 | Martin et al. |
| 6,530,944 | B2 | 3/2003 | West et al. |
| 6,534,443 | B2 | 3/2003 | Inuzuka |
| 6,547,146 | B1 | 4/2003 | Meksavan et al. |
| 6,590,647 | B2 | 7/2003 | Stephenson |
| 6,623,786 | B2 | 9/2003 | Baron et al. |
| 6,645,517 | B2 | 11/2003 | West et al. |
| 6,660,381 | B2 | 12/2003 | Halas et al. |
| 6,685,730 | B2 | 2/2004 | West et al. |
| 6,685,986 | B2 | 2/2004 | Oldenburg et al. |
| 6,699,724 | B1 | 3/2004 | West et al. |
| 6,765,211 | B2 | 7/2004 | Tapalian et al. |
| 6,778,316 | B2 | 8/2004 | Halas et al. |
| 6,827,453 | B2 | 12/2004 | D'Alessio et al. |
| 6,852,252 | B2 | 2/2005 | Halas et al. |
| 6,867,421 | B1 | 3/2005 | Hunt et al. |
| 6,899,707 | B2 | 5/2005 | Scholler et al. |
| 6,908,496 | B2 | 6/2005 | Halas et al. |
| 6,914,086 | B2 | 7/2005 | Hong |
| 6,919,988 | B2 | 7/2005 | Cook |
| 6,989,007 | B2 | 1/2006 | Shadduck |
| 7,019,391 | B2 | 3/2006 | Tran |
| 7,057,732 | B2 | 6/2006 | Jorgenson et al. |
| 2002/0187347 | A1* | 12/2002 | Halas et al. ............... 428/403 |
| 2005/0209666 | A1* | 9/2005 | Hunter et al. ............... 607/115 |
| 2005/0211930 | A1* | 9/2005 | DeMeo et al. ............ 250/516.1 |
| 2005/0265935 | A1* | 12/2005 | Hollingsworth et al. ....... 424/59 |

* cited by examiner

PLASMON RESONANT BASED EYE PROTECTION

This application claims priority to U.S. provisional application No. 60/678,754 filed on May 7, 2005.

STATEMENT REGARDING FEDERALLY SPONSORED RESEARCH OR DEVELOPMENT

The work leading to the invention received support from the United States federal Government under SBIR Grant, Contract No. F08650-05-M-6598. The federal government may have certain rights in this invention.

BACKGROUND OF THE INVENTION

1. Field of the Invention

The present invention relates to compositions and methods for the protection of vision from incident electromagnetic radiation using plasmon resonant particles. More particularly, the invention relates to infrared radiation extinguishing eye protection and a process for producing infrared radiation extinguishing eye protection utilizing plasmon resonant particles. Most particularly, the invention relates to infrared radiation extinguishing contact lenses and a process for producing infrared radiation extinguishing contact lenses utilizing optically tunable nanoshells.

2. Prior Art

Eye exposure to certain portions of the electromagnetic spectrum is known to be damaging to the cornea and to be the cause of several ocular pathologies. More specifically, while the visible light portion of the spectrum ranges from approximately 400-700 nm, those portions of the energy spectrum adjacent to visible light, namely ultraviolet radiation (approximately 200-400 nm), and infrared radiation (approximately 670-1200 nm) are known to be harmful to the eyes.

The need for these eye protection devices results from the hazard to the eye from extended exposure to solar radiation (either at sea level, at other altitudes or in space) or artificially generated electromagnetic radiation, such as lasers. Broad protection from the solar radiation can be effected by devices that provide substantial extinction across many wavelengths. The focusing mechanism of the eye will concentrate incident light on the retina. This focusing effect can result in retinal damage, either temporary or permanent, from electromagnetic radiation. If the incident electromagnetic radiation is not visible to the eye, such as in the near infrared, damage can occur without awareness of the incident light.

Devices for protecting the eye from incident light include goggles, glasses, contact lenses and similar devices. Moreover, certain devices have been designed and developed to extinguish ultra-violet, visible, near-infrared or other wavelengths.

Generally, films, reflective surfaces or additives have been used in these devices to alter eye color or appearance by selectively reflecting or absorbing different wavelengths. Additionally, these techniques have been used to selectively diminish or extinguish some or most of the incident light across a broad area of the solar spectrum, such as in traditional sunglasses.

One area where exposure to infrared radiation is of particular concern is through the use of lasers in military applications. The current most common laser eye protection is goggles. However, when used by combat forces, goggles can pose integration problems by interfering with other equipment. In many cases, it is difficult or impractical to integrate such goggles with these other pieces of equipment, and the use of goggles or glasses allows the potential for reflected incident electromagnetic radiation to reach the eye. These integration issues have led many soldiers who require traditional vision corrective glasses to wear contact lenses. Therefore, it would be desirable to provide contact lenses that are capable of extinguishing infrared radiation.

Considerable attention has focused in the prior art on providing glasses and contact lenses capable of absorbing or reflecting ultraviolet radiation in order to protect the eyes. In particular, it is well known in the art to add UV-absorbing compounds to a contact lens polymer or to otherwise provide a dye or color additive to the lens in order to block ultraviolet light. Heretofore, little attention in the prior art has focused on protecting the eyes from infrared radiation. Part of this is due to the fact that normal eye exposure to infrared radiation is much less intense than eye exposure to ultraviolet radiation. Shorter wavelengths have higher energy levels and are more commonly absorbed by human tissue, resulting in a higher potential for damage. Infrared radiation in solar radiation has a lower level of intensity as well as a lower energy level, and generally is less damaging to the eye or tissue. Higher intensity infrared radiation is most commonly associated with lasers. Moreover, unlike UV-absorbing agents, there are very few substances known to absorb infrared radiation and remain relatively transparent in the visible. Those skilled in the art will understand that while carbon does in fact absorb infrared radiation, it is otherwise undesirable because it also absorbs light from other parts of the energy spectrum, including visible light, therefore reducing the ability to selectively extinguish certain wavelengths while maintaining transmission in other wavelengths.

Colored or tinted contact lenses are commonly used to alter eye color for cosmetic reasons, but do not offer selective wavelength protection. Tinted lenses employ dyes or other additives to provide color without completely blocking the passage of visible wavelengths through the lens. These techniques are generally designed to avoid coloration of the pupil to create a natural appearance. Examples of these lenses are described in U.S. Pat. Nos. 4,468,229; 4,460,523, 4,447,474; 4,355,135; 4,252,421; 4,157,892; 3,962,505; 3,679,504 and 2,524,811.

Reflective coatings have also been described to reflect specific wavelengths to provide a color change to the iris of the eye, an example of which is described in U.S. Pat. No. 6,164,777.

U.S. Pat. No. 4,669,834 describes the use of reflective material to protect the eye from electromagnetic radiation, including infrared wavelengths, wherein such reflective material included metal particles, such as gold, platinum, stainless steel, silver, nickel, chrome, aluminum, and nickel alloys; other particulate matter, including ground oyster shells and mica. The specifications do not provide the optical properties of the materials described, which are well-known to provide the most significant extinction in the visible spectrum. In general, these metal particles have a plasmon resonance and will extinguish light principally in the visible wavelengths. The extinction properties of these particles are generally narrow, if the particle is smaller than the incident wavelength, or broad across the visible spectrum if the particle is large. The construction of particular plasmon resonant particle using these materials to extinguish selective wavelengths was not described.

U.S. Pat. No. 5,112,883 describes the use of melanin, a biological molecule, as an absorbing pigment for radiation protection. The extinction spectrum of melanin as described and as known to those of ordinary skill is principally in the visible spectrum, with limited absorption in the near infrared, and limited ability to alter the absorption spectrum if desired to selectively extinguish wavelengths.

These traditional approaches to design and manufacture of contact lenses and other protective eyewear involve protection from radiation intensities common in solar radiation and from reflection of such radiation. Some methods are used to provide protection from more intense radiation. U.S. Pat. No. 4,848,894 describes a method for eye protection from high-intensity optical radiation such as that from a laser. The invention contemplates the use of thin films, reflectors, filters or absorbing dyes. The degree and wavelength of protection described is inherent in the particular properties of the materials described.

The recent development of plasmon resonant particles can contribute significantly to the field of eye protection. While traditional protective techniques have varying levels of stability and selectivity for vision protection, plasmon resonant particles offer the ability to selectively extinguish, either by absorption or scattering, electromagnetic radiation in a broad range of the electromagnetic spectrum. Additionally, these materials can be produced in a biocompatible format to avoid damage to the eye when in close contact, such as in a contact lens format.

Plasmon resonant particles are generally metallic particles which efficiently scatter optical light elastically because of a collective resonance of the conduction electrons in the metal. The magnitude, bandwidth and extinction peak of the plasmon resonance associated with a particle are dependent on the size, shape, structure and composition of the particle. These factors are also affected by the environment in which the particle is placed. Generally, the optical properties of a plasmon resonant particle can be significantly different than solid material. For example, materials of a particular shape can have significantly different optical properties than materials of a similar shape but different size or of a similar size but different composition or of a similar shape but different composition.

As plasmon resonant particles were first manufactured, the possibility of using such materials for extinguishing selective wavelengths was contemplated. In U.S. Pat. No. 6,344,272, Oldenburg et al indicated that the selective infrared absorption of their plasmon resonant particles, metal nanoshells, may be useful for laser eye protection, or eye protection from other potentially damaging sources of infrared radiation. However, the authors did not describe the particles required for such application or the methods of preparation of the protective eyewear.

Subsequently, it has been demonstrated that plasmon resonant particles can be embedded in polymers or materials for different applications. U.S. Pat. Nos. 6,645,517 and 6,428,272 describe methods for including plasmon resonant particles in polymers for drug delivery and as a light-activated device. U.S. Pat. No. 6,852,252 describes the use of plasmon resonant particles to change the rate of photo-oxidation of polymers.

Plasmon resonant particles are available in many forms. One such form is a metal nanoshell, as more fully described in U.S. Pat. No. 6,344,272, incorporated herein by reference. Another such form is a nanorod, as described in Journal of Physical Chemistry B, Volume 103, pg. 3073, (1999). Other forms include stars (Nanoletters, Volume 6, pg. 683 (2006), cubes, elliptical particles, as described in the enormous amount of literature. For a review see Optical Properties of Metal Clusters by Kreibig and Volmer, Springer-Verlag (1995). A common trait of plasmon resonant particles is the ability to manufacture such particles to have desired optical properties, including extinguishment of electromagnetic radiation in various parts of the spectrum. Those skilled in the art will appreciate that protective eyewear may be comprised of plasmon resonant particles selected from among various sizes, shapes and compositions.

With this in mind, those skilled in the art will appreciate that a contact lens must be functional and biocompatible, with different requirements than goggles or glasses. The appropriate characteristics of a good contact lens include oxygen permeability, wettability, material strength, and stability. These factors must be carefully balanced to achieve a useable contact lens. Oxygen permeability is paramount since the cornea receives its oxygen supply exclusively from contact with the atmosphere. Tear fluid wettability keeps the contact lubricated, allowing it to be worn comfortably on the eye.

Contact lenses are typically hydrogels, a hydrated crosslinked polymeric system that contains water in an equilibrium state. In general, as the water content increases, the oxygen permeability also increases. These hydrogels are typically comprised of copolymers of N-vinyl-pyrolidone and methyl methacrylate, which have water content in the 70-80% range.

Accordingly, any modification to a contact lens to provide infrared wavelength protection must not alter the biocompatibility, wettability, or oxygen permeability. In addition, any embedded material must be stable, not oxidize, and be easily embedded in a polymeric system.

SUMMARY OF THE INVENTION

The present invention relates to compositions and methods for the protection of vision from incident electromagnetic radiation using plasmon resonant particles. The varying optical properties of plasmon resonant particles are used to selectively absorb or extinguish wavelengths in eyewear to minimize damage to the eyes from incident electromagnetic radiation. The desired parameters of vision protection can be determined through the selection from among plasmon resonant particles with different properties, the engineering design of such particles, the composition of mixtures of such particles, and the density of such particles within the device. Each of these is a controllable parameter that may be altered to select the desired level of vision protection from a specified wavelength. Specifically, the eyewear may be goggles, glasses, contact lenses or the like. Such device could also be an implant. In one embodiment, the invention relates to infrared radiation extinguishing eyewear, and more particularly, to contact lenses and a process for producing infrared radiation extinguishing contact lenses utilizing plasmon resonant particles. Preferably, the plasmon resonant particles are optically tunable nanoshells. In another embodiment, the invention relates to the addition of plasmon resonant particles to dyes, films or other additives or layers to provide additional protection to existing eyewear devices.

Plasmon resonant particles in general, and nanoshells in particular, may be designed and consistently manufactured with peak plasmon resonances at desired wavelengths, including the near-infrared. A nanoshell is a nanoparticle consisting of a dielectric core and a metal shell. Plasmon resonance frequency is determined by the relative size of the core and the metal shell. With the capability to alter the relative size of the core and the metal shell, nanoshells are uniquely tunable nanoparticles, allowing a range of optical extinctions. While the invention primarily focuses on protective eyewear with nanoshells tuned to absorb infrared energy wavelengths, those skilled in the art will understand that the nanoshells may be fabricated in order to absorb other energy wavelengths, or other plasmon resonant particles may be fabricated to absorb infrared wavelengths.

Contact lenses are manufactured by spincasting processes, cast molding processes, or a combination of these two methods. In one desired embodiment of the invention, the plasmon resonant particles are introduced into the lens polymer prior to the particular lens manufacturing process. In another embodiment of the invention, the plasmon resonant particles are coated on a contact lens after formation of the lens.

The varying optical properties of plasmon resonant particles are used to selectively absorb or extinguish wavelengths to minimize damage to the eye from incident electromagnetic radiation. The desired parameters of vision protection can be determined through the selection from among plasmon resonant particles with different properties, the engineering design of such particles, the composition of mixtures of such particles, and the density of such particles within the device. Each of these is a controllable parameter that may be altered to select the desired level of vision protection from a specified wavelength.

DESCRIPTION OF THE PREFERRED EMBODIMENTS

Figure 1:
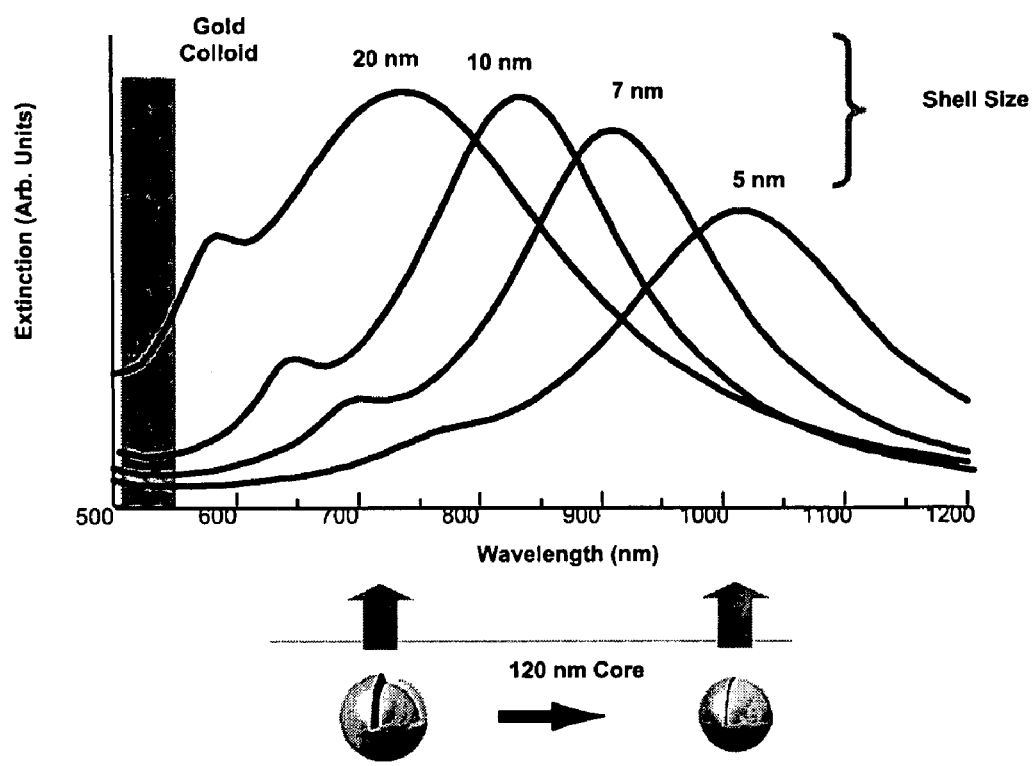
FIG. 1 illustrates the optical shift in a nanoshell based on the ratio of shell thickness to core size for a particular nanoshell size and composition.

It has been found that by incorporating nanoshells in the manufacture of a contact lens, various wavelengths of energy, and in particular, near-infrared radiation wavelengths, can be filtered or otherwise blocked from passing through the lens.

Nanoparticles and materials formed therefrom, referred to herein as nanomaterials, constitute an emerging subdiscipline in the chemical and materials science arts. While there is no universally agreed upon definition of when a small particle qualifies as a nanoparticle, particles with at least one dimension (d)≦100 nm are generally considered nanoparticles. As used herein, nanoparticles includes particles with one dimension less than a micron. Further, in the preferred embodiment, the most desirable nanoshells are >100 nm. In any event, those skilled in the art generally acknowledged that various properties of a material change as the particle size approaches molecular dimensions. It is these unique properties of the nanomaterial that make it useful for various applications.

Moreover, solid metal nanoparticles (i.e. solid, single metal spheres of uniform composition and nanometer dimensions) are known to possess unique optical properties. In particular, metal nanoparticles (especially the coinage metals) display a pronounced optical resonance. This so-called plasmon resonance is due to the collective coupling of the conduction electrons in the metal sphere to the incident electromagnetic field. This resonance can be dominated by absorption or scattering depending on the dimensions of the nanoparticle with respect to the wavelength of the incident electromagnetic radiation. Associated with this plasmon resonance is a strong local field enhancement in the interior of the metal nanoparticle. A serious practical limitation to realizing many applications of solid metal nanoparticles is the inability to position the plasmon resonance at technologically important wavelengths. Solid nanoparticles, such as gold and silver, absorb light in the optical regions of the human. For example, solid gold nanoparticles of 10 nm in diameter have a plasmon resonance centered approximately at 520 nm. This plasmon resonance cannot be controllably shifted by more than approximately 100 nanometers by varying the particle diameter or the specific embedding medium.

A new class of nanoparticles has recently emerged wherein a non-conducting inner layer is coated with a layer of conducting material, thereby forming a conducting shell around a non-conducting core. These materials may be spherical, ellipsoidal, or other shapes. These nanoparticles are referred to as nanoshells and have been demonstrated to have capabilities of absorbing electromagnetic radiation maximally at wavelengths in the visible or infrared regions of the electromagnetic spectrum. In one preferred embodiment of the invention, nanoshells are formed of a silica core and a gold or silver shell.

Moreover, the ratio of shell thickness to core size dictates the optical shift or absorption capabilities of the nanoshell. In a concentric geometry such as a nanoshell, this absorption is shifted to higher wavelengths. Thus, compared to solid nanoparticles that have static optical extinctions, nanoshells have dynamic optical extinctions that can be tuned as desired. By adjusting the relative core diameter or size and shell thicknesses, gold and silver nanoshells can be fabricated that will absorb or scatter light at various wavelength along the electromagnetic spectrum, particularly in the visible and infrared regions.

FIG. 1 illustrates a nanoshell's optical shift as the ratio of shell thickness to core size is altered. In the illustration a 120 nm diameter silica core is utilized. Different shell thicknesses ranging from 20 nm to 5 nm are shown. Keeping the core diameter constant, as the shell thickness decreases, the plasmon resonance peak shifts from lower frequency wavelengths to higher frequency wavelengths along the energy spectrum. The bar on the left illustrates the very narrow band of wavelengths extinguished by solid metal nanoparticles.

Theoretically, the plasmon resonance of metal nanoshells is governed by Mie scattering theory. Mie scattering has accurately described the plasmon resonance of gold nanoshells, silver nanoshells, and electromagnetic contributions to the surface enhanced Raman response. The plasmon resonance of a core shell structure is determined by the physical dimensions and the optical dielectric properties of the core, shell, and medium.

Figure 2:
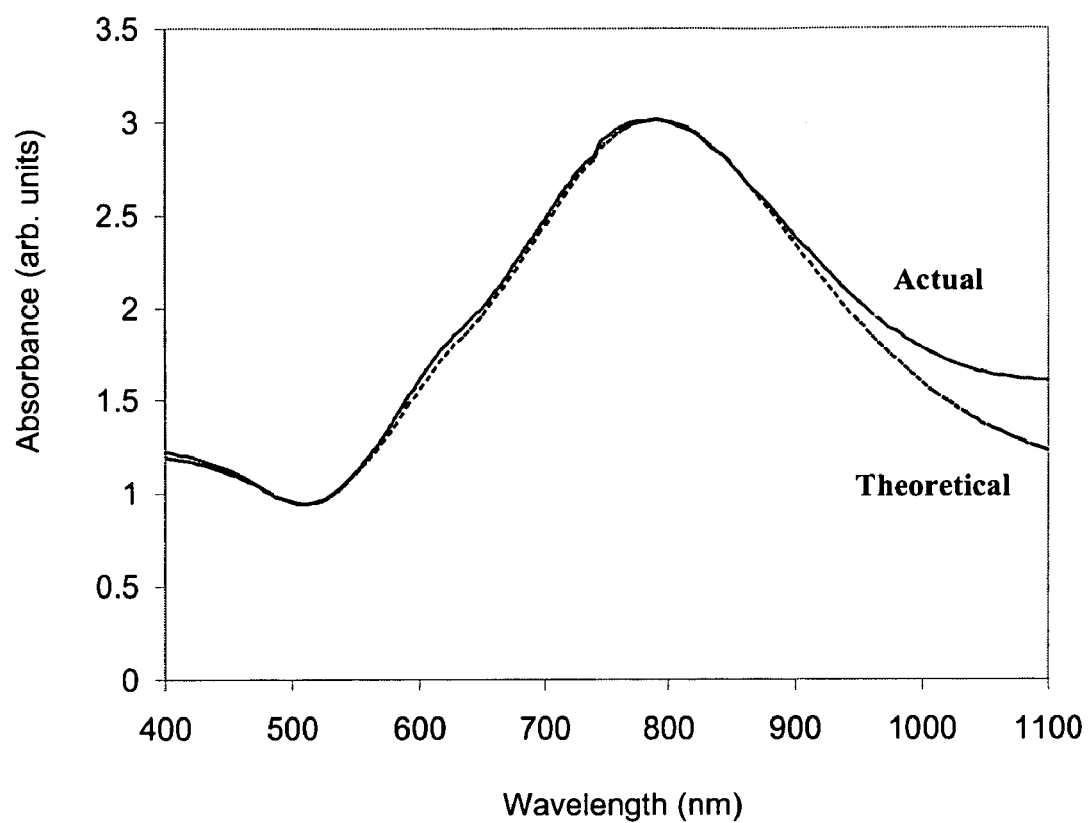
FIG. 2 illustrates the high correlation between predicted and observed optical properties for a nanoshell of specified dimensions and materials.

With reference to FIG. 2, it can be seen that there is a high correlation between the observed and theoretical optical properties of nanoshells. FIG. 2 shows a calculated Mie scattering spectrum (dashed line) and the corresponding measured spectrum of an "off the shelf" nanoshell solution (solid line) characterized by UV/VIS spectra of a gold nanoshell solution with a silica core radius of 58 nm and a 13 nm gold shell dispersed in water. The correlation between the measured and calculated optical response of nanoshells has been verified extensively. As indicated, there is a high correlation between predicted and observed optical properties for a nanoshell of specified dimensions and materials. While this is not the ideal nanoshell for a contact lens, this nanoshell effectively filters out 750-900 nm while allowing optical clarity.

Because of this close correlation with the Mie scattering theory, demonstrated in FIG. 2, the optical properties of a particular nanoshell can be predicted during the design phase. Currently, gold and silver nanoshells can be reproducibly fabricated with a silica core ranging from 80-500 nm in diameter with shell thickness ranging from 7-35 nm. As illustrated by FIG. 1, this allows for a tuning range from 630-2500 nm, covering the visible and infrared regions of the electromagnetic spectrum. The use of other materials will allow nanoshells of different dimensions, with diameters smaller than 80 nm, and with extinction properties ranging from the visible through far infrared.

While various substances may be utilized to construct the outer shell of a nanoshell utilized in the invention, in one preferred embodiment the outer shell is formed of gold. Gold nanoshells are uniquely suited for laser eye protection in a contact lens format. Gold is biocompatible, so there are no toxicity concerns, and gold nanoshells have a characteristic dip in the plasmon resonance at the maximum efficiency of the human eye. Further, the optical cross-section of a particular nanoshell may be significantly larger than the physical cross-section at the plasmon resonance peak in the near-infrared, allowing the particle to absorb significant light relative to dyes and other particles.

In another embodiment of the invention, other plasmon resonant particles can provide similar optical shifts. For example, nanorods, when linearly polarized light is aligned along the long axis of the rod, can absorb near-infrared wavelengths. However, nanoshells, as a spherical material, avoid the concerns inherent in attempting to achieve infrared protection with polarization dependence. As another example, "hollow" nanoparticles have been produced that have similar optical properties. See "Metal nanostrcutures with hollow interiors", Sun, Y G; Mayers, B; Xia, Y N, ADVAN MATER, Volume: 15, Apr. 17, 2003, pages 641-646. These materials may be spherical or other shapes.

Contact lens manufacturing generally involves the production of a solid cylinder (a "blank") from which disks are cut and lathed into lenses. The disks are manufactured by spin-casting processes, cast molding processes, or a combination of these two methods. The blanks are formed from the polymerization of the monomers.

Figure 5:
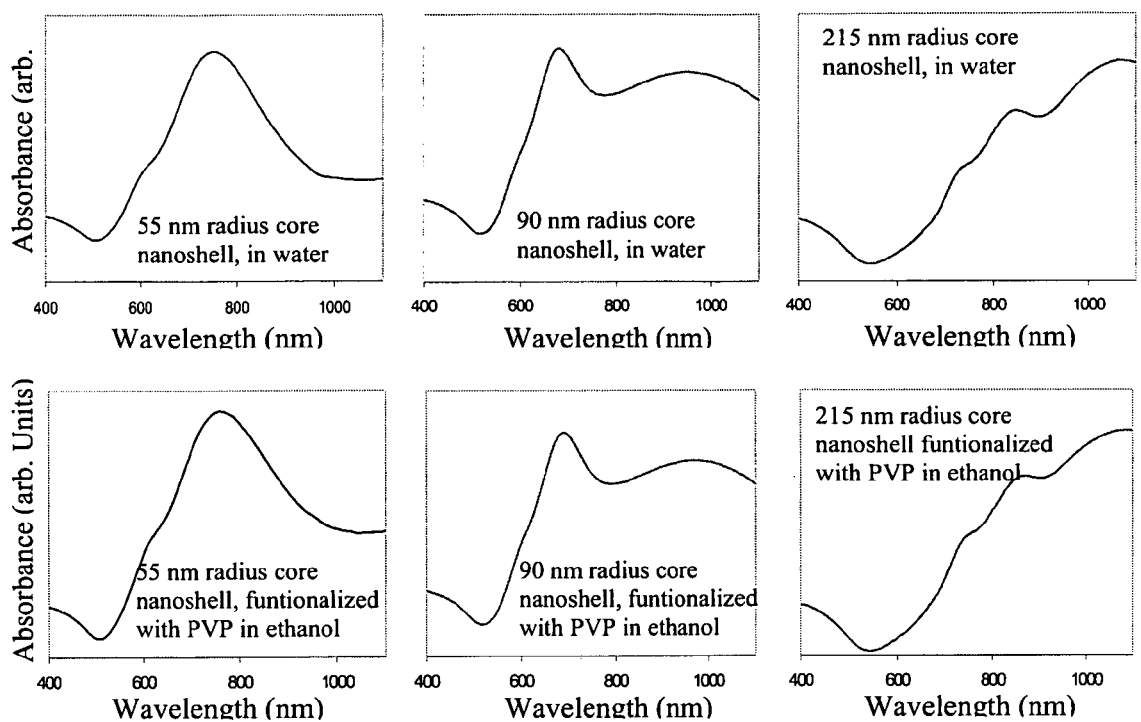
FIG. 5 illustrates the extinction spectra of three different core-radii nanoshell compositions immersed in water as compared to the same particles functionalized with PVP and dispersed in ethanol.

In one preferred embodiment of the invention, the nanoshells are deposited in the polymers for contact lenses. The nanoshells are manufactured as usual, and then functionalized with polyvinylpyrrolidone (PVP) or polyvinylalcohol (PVA). These coatings create a protective layer of the nanoshells that allows them to be centrifuged and redispersed into organic solvents, such as ethanol or toluene, and saline. See FIG. 5.

Figure 6:
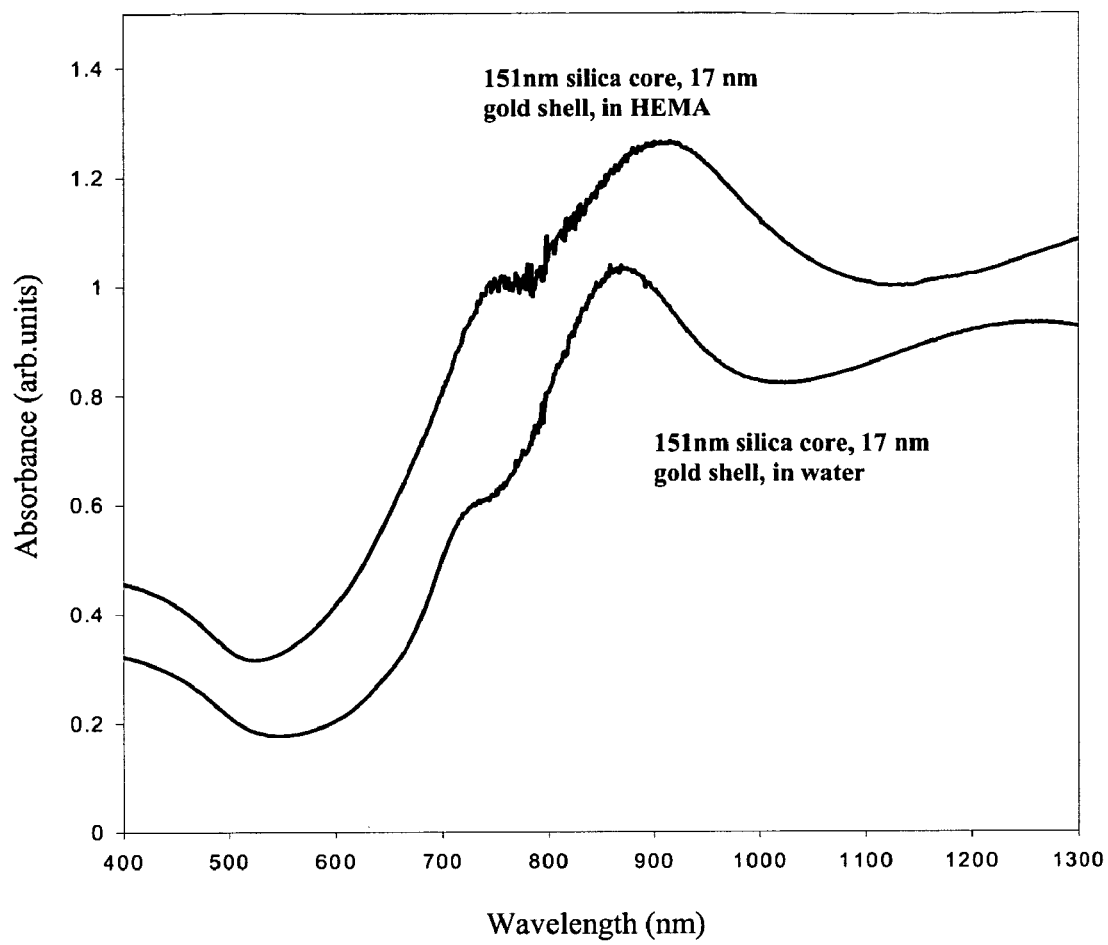
FIG. 6 illustrates the extinction spectra of a nanoshell solution dispersed in water versus the same nanoshells dispersed in HEMA, a common contact lens monomer.

In another embodiment of the invention, shown in FIG. 6, nanoshells were dispersed in 2-hydroxyethylmethacrylate (HEMA), a popular monomer in the contact lens manufacturing process, without the use of a protective PVP or PVA layer.

Given the low (0.11%) amount of nanoshells present, there are minimal changes in the polymerization process as a result of the presence of nanoshells. In fact, the standard contact lens absorbed on average 55% water without nanoshells and 60% water with nanoshells. The presence of nanoshells tends to slightly improved hydration.

Further, it has been observed that there is a characteristic red shift in the plasmon resonance of the nanoshells as a result of the increase in the optical dielectric constant of the monomer solution as compared to water (see FIG. 6). However, most soft contact lenses are greater than 50% water after post processing, the result being that the plasmon resonance shifts back closer to the nanoshell plasmon resonance in water in the final product. Alternatively, the nanoshell core and shell geometry can be modified to compensate for this shift.

Those skilled in the art will appreciate that the nanoshell concentration can easily be adjusted to compensate for different lens thickness, and hence different contact lens prescriptions, or desired thickness with no prescription.

In either case, the foregoing is preferred because the plasmon resonant nanoshell can easily be incorporated into the current manufacturing processes of contact lenses that are based on polymer technologies. Significantly, because the nanoshells are incorporated prior to the implementation of the cutting and lathing process, there is only minimal modification to manufacturing.

The foregoing invention is also economically feasible. The physical amount of gold in a nanoshell solution is extremely small. While higher concentrated solutions and greater extinction are feasible, in one desired embodiment, the concentration of nanoshells is less than 0.15% by volume. As an example, one nanoshell solution has a silica core radius of 151 nm and a 17 nm thick gold shell. Given a relatively large contact lens blank of 14.5 mm diameter and 1 cm thickness, to achieve a desired nanoshell optical density, the nanoshell concentration is $5.5 \times 10^{10}$ particles/ml. This contact lens would be 0.11% nanoshells by volume. Thus, the cost of gold in this contact lens blank is negligible.

Nanoshells have the added benefit that they remain stable in a saline environment in a similar fashion via polyvinylalcohol (PVA) with minimal effect on the plasmon resonance. PVA has been previously used to coat implants and MRI contrast agents. The standard method for manufacturing soft contact lenses following the initial polymerization and cutting is to soak the contact lens in a saline solution. Contact lenses are also stored in a saline solution.

With further reference to FIG. 2, it can be seen that each nanoshell has an extinguishing curve that can be characterized by a peak and a trough, which can be expressed as a peak to trough ratio. The peak to trough ratios of typical nanoshell solutions varies from 2 to 7. A higher peak to trough ratio allows the maximum protection in the near-infrared regions and the maximum transmission in the visible spectrum. Given a constant shell thickness, the peak-to-trough ratio increases as the core radius increases, and the resultant plasmon resonance moves towards the infrared. Given a constant core radius, the peak-to-trough ratio decreases with increasing shell thickness, and the plasmon resonance moves towards the visible. The peak-to-trough ratio and the plasmon resonance shift are more sensitive to core radius changes than shell thickness changes. Given this trend, the peak-to-trough ratio of the nanoshell responsible for blocking the 670-850 nm range will determine the overall transmission in the visible range of the human eye.

In an illustrative example, the peak to trough ratio of a nanoshell having a silica core radius of ~151 nm and a gold shell thickness of 17 nm yields a peak-to-trough ratio that extinguished the 670-850 nm range.

Figure 4:
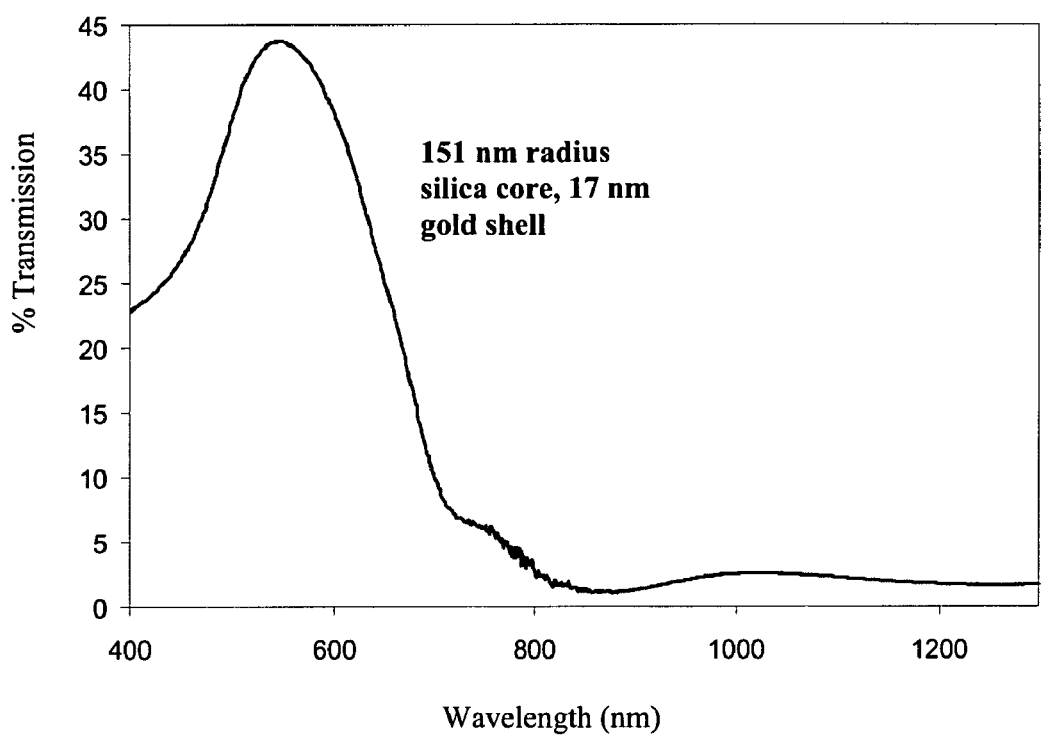
FIG. 4 illustrates the percent transmission of a nanoshell solution taken in a 0.2 mm pathlength cuvette.

The extinction cross-section (in m²) can also be calculated as a function of core radius and shell thickness. The optimal nanoshell for a partial region of the energy spectrum, regardless of concentration (since altering the concentration moves the entire curve up and down) is as follows:

In one embodiment, the optimal nanoshell for extinguishing the light from 670-850 nm wavelength, while allowing the most transmittance in the visible range of 400-670 nm, has a core radius of approximately 151 nm and a shell thickness of approximately 17 nm, an example of this is shown in FIG. 4.

In one embodiment, the optimal nanoshell for extinguishing the light from 1030-1200 nm, while allowing the most transmittance in the visible range of 400-670 nm, has a core radius of 370 nm and a shell thickness of 15 nm.

In one embodiment, the optimal nanoshell for extinguishing the light from 850-1030 nm, while allowing the most transmittance in the visible range of 400-670 nm, has a core radius of 300 nm and a shell thickness of 17 nm.

In other non-limiting embodiments, suitable core radius' range from 58 to 215 nm with varying shell thicknesses.

In another embodiment of the invention, the nanoshells are deposited on at least one surface of the manufactured lens, or alternatively, on both the front and back surfaces of the lens. Those skilled in the art will appreciate that this method is less desirable because it adds and additional step to the manufacturing process.

A contact lens is typically 0.19 mm to 0.4 mm thick. We tested the Lambert-Beer absorption law for this short pathlength to provide a general idea of the concentration of nanoshells needed to achieve desired optical characteristics, and to test the validity of the Lambert-Beer law at these concentrations and pathlengths. Cuvettes with 0.2 mm and 0.5 mm pathlengths were used. Using these cuvettes, as well as our standard 1 cm pathlength cuvettes, the optical response of the same nanoshell solution as described in FIG. 1, with different concentrations, was used to test the Lambert-Beer absorption law. The results are shown in FIG. 4.

Figure 3:
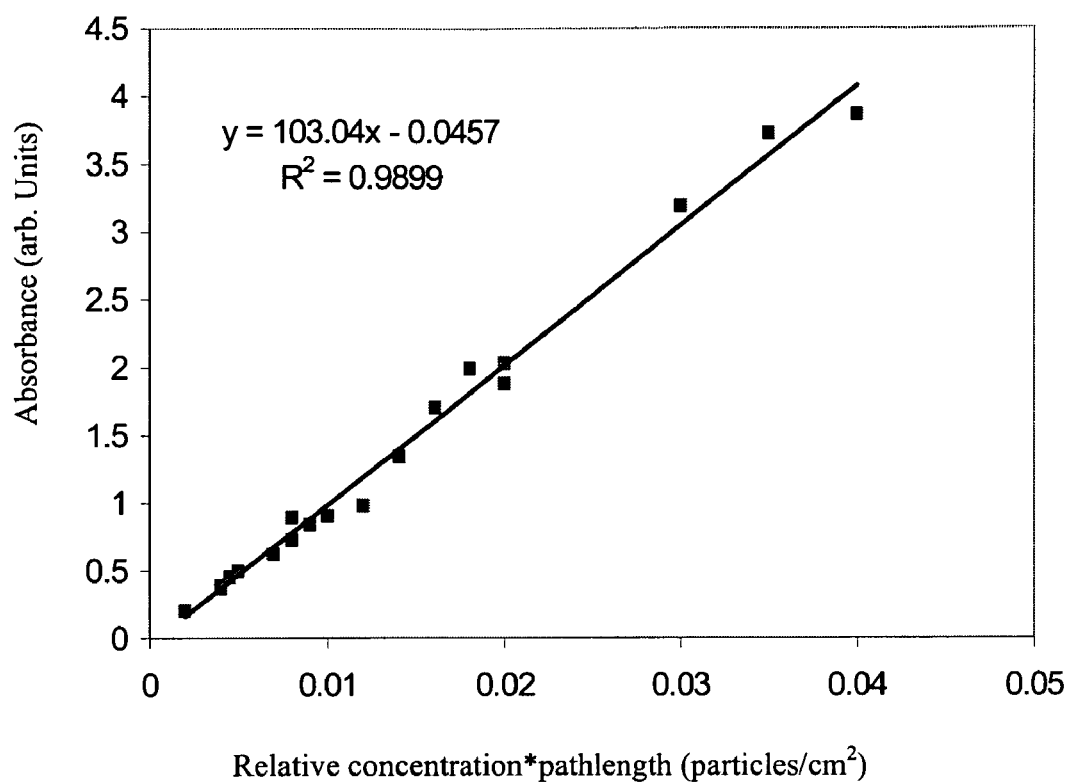
FIG. 3 illustrates the extinction of various concentrations and pathlengths of nanoshells confirming Lambert-Beer's Law for the pathlengths and nanoshell concentrations.

The optical characteristics of the nanoshells demonstrated in FIG. 3 were measured in 0.2 mm and 0.5 mm pathlength cuvettes (typical contact lens thickness) to determine the appropriate nanoshell concentration. The percent transmission of the 0.2 mm cuvette is shown in FIG. 4. The desired concentrations were determined to be $5.5 \times 10^{10}$ nanoshell/ml and $2.21 \times 10^{10}$ nanoshells/ml for the 0.2 mm and 0.5 mm pathlength cuvettes, respectively, which achieved extinction of greater than 95% in the near-infrared spectrum. These concentrations represent less than 0.15% by volume of nanoshells. Higher concentrated solutions and greater extinction are feasible. These measurements were taken from nanoshell solution dispersed in water.

A protocol was established for the incorporation of nanoshells into polymers. The nanoshells are manufactured as usual, and then functionalized with polyvinylpyrrolidone (PVP) or polyvinylalcohol (PVA). These coatings create a protective layer of the nanoshells that allows them to be centrifuged and redispersed into organic solvents, such as ethanol or toluene, and saline. This process is demonstrated in FIG. 5.

We purchased 2-hydroxyethylmethacrylate (HEMA), a popular monomer in the contact lens manufacturing process, and it was discovered that nanoshells can be dispersed in this monomer easily, without the use of a protective PVP or PVA layer. This is demonstrated in FIG. 6.

There is a characteristic red shift in the plasmon resonance of the nanoshells as a result of the increase in the optical dielectric constant of the monomer solution as compared to water. However, most soft contact lenses are greater than 50% water after post processing. We expected the plasmon resonance to shift back closer to the nanoshell plasmon resonance in water in the final product. However this is not the case, the core and shell geometry can be modified to compensate.

Figure 7:
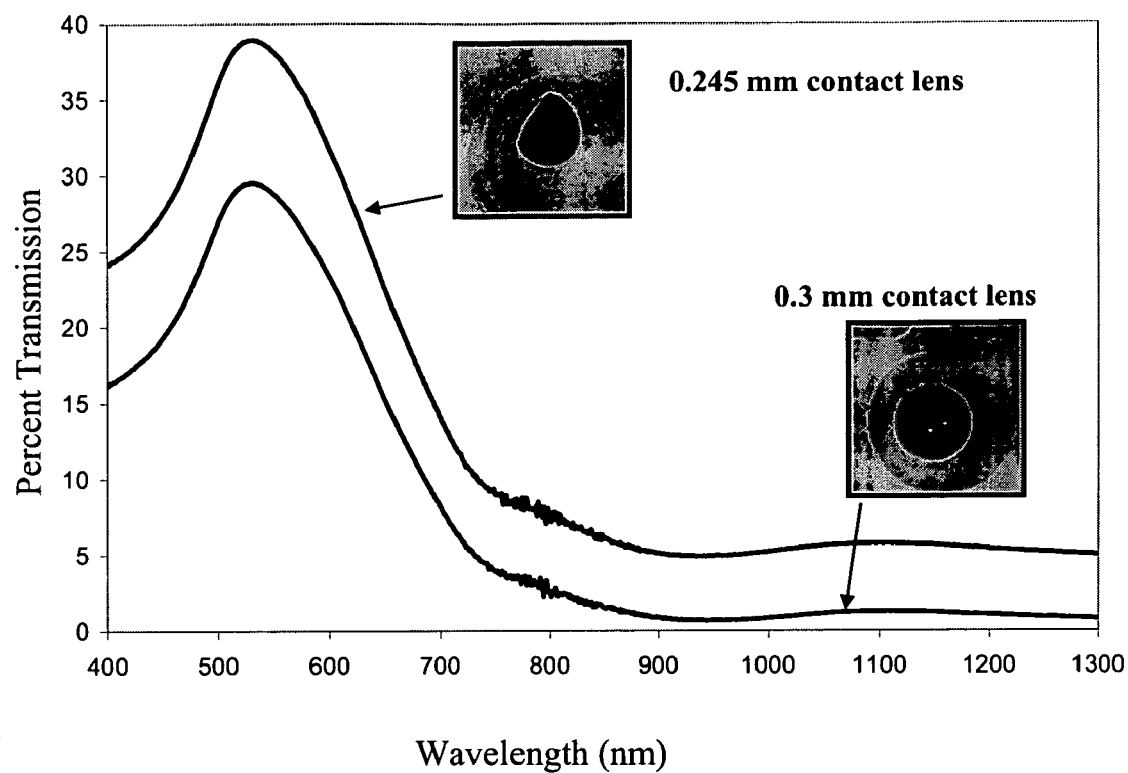
FIG. 7 illustrates the spectra and photographic images of two nanoshell-embedded contact lens prototypes.
Figure 8:
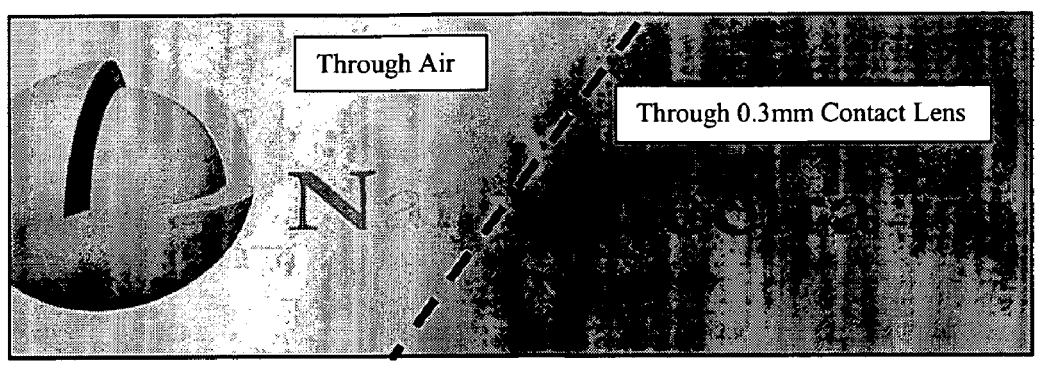
FIG. 8 illustrates the clarity of a digital camera image taken partially through the 0.3 mm contact lens described in FIG. 7 as compared to the portion of the photo taken through air.

A 0.254 mm and a 0.3 mm contact lens were produced and one was polished to a strong, near-sighted prescription. There were no problems noted in the polishing process. These contact lenses are illustrated in FIG. 7. The nanoshell concentration can easily be adjusted to compensate for different lens thickness, and hence different contact lens prescriptions, or desired thickness with no prescription. FIG. 8 is a photo taken through the 0.3 mm contact lens, illustrating clarity.

Figure 9:
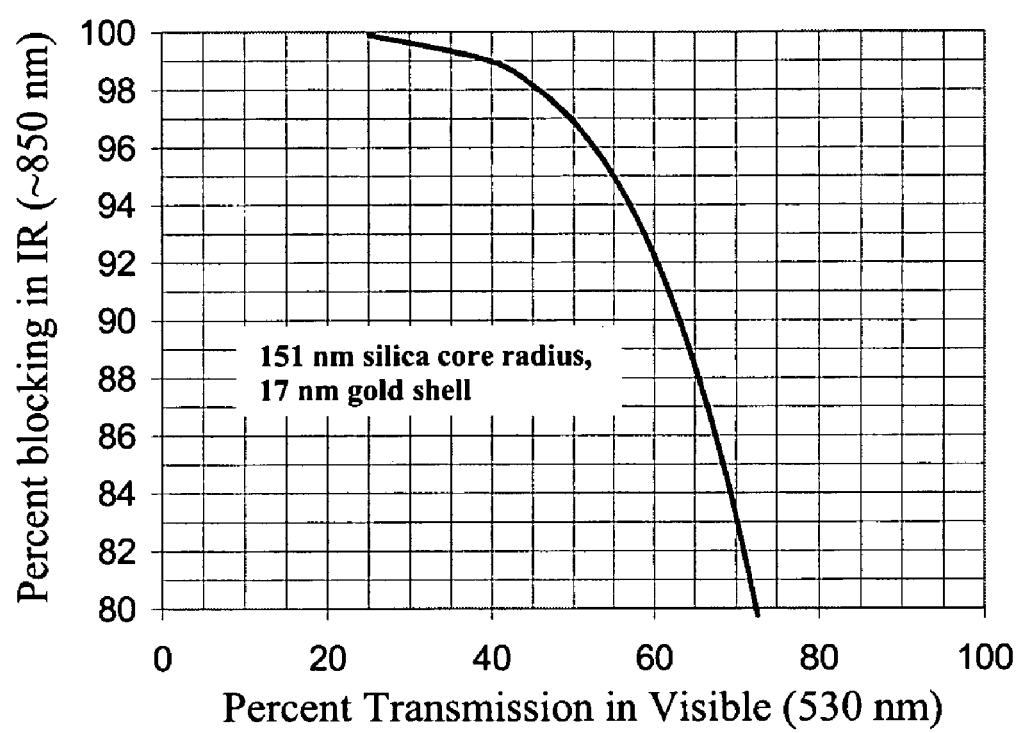
FIG. 9 is a graphical illustration of the performance of nanoshell embedded soft contact lens.

FIG. 9 illustrates the flexibility of production of contact lenses using plasmon resonant particles, using 530 nm in the visible (the wavelength of high sensitivity of the human eye) and ~850 nm in the near infrared. As illustrated in FIG. 9, to achieve 30% transmission at 530 nm, 99% protection at the 850 nm wavelength can be achieved. 90% protection at this wavelength would result in approximately 60% transmission. Similar comparison can be made from this graphical illustration.

The foregoing tunable nanoshell-based contact lens as described herein blocks harmful wavelengths while allowing high luminescence in visible spectra. The lenses are particularly useful in delivering protection in the region of 670 nm to 1200 nm. Additionally, these plasmon resonant nanostructures embedded in a contact lens will have no haze, distortion, aberration, prism, or artifacts that impair visual performance or create distractions the visual field. The performance of the lens can be adjusted to meet the customer specifications, within the limits of the intrinsic properties of the materials. Moreover, the concentration of the nanoshells can easily be increased to block>99% in the infrared region, while remaining relatively transparent in the visible range, wherein the transmission exceeds that of an average pair of sunglasses.

Nanoshells have been demonstrated to be relatively inexpensive to manufacture and have a high safety profile when used in vivo. This is particularly true of gold nanoshells. The forgoing process described herein is also desirable because it results in little to no interference in the current contact lens manufacturing techniques.

While the included references describe the method of inclusion of nanoshells into a contact lens, one of ordinary skill will recognize that a similar process can be used for inclusion of nanoshells in plastics or other materials for inclusion in other protective eyewear. Additionally, the process for inclusion of nanoshells in protective eyewear will also allow the inclusion of other plasmon resonant particles such as nanorods, hollow nanoparticles, etc.

While certain features and embodiments of the invention have been described in detail herein, it will be readily understood that the invention encompasses all modifications and enhancements within the scope and spirit of the following claims.

What is claimed is:

1. A device to reduce electromagnetic radiation entering the eye, comprising:
   eyewear; and
   plasmon resonant particles, embedded in said eyewear, wherein said plasmon resonant particles are characterized by a plasmon resonant peak in the electromagnetic frequency range between 670 nm and 1200 nm.

2. The device of claim 1, wherein the plasmon resonant particles are nanoshells.

3. The device of claim 1, wherein the plasmon resonant particles are nanorods.

4. The device of claim 1, wherein the plasmon resonant particles are nanotubes.

5. The device of claim 1, wherein the plasmon resonant particles comprise a non-conducting core and at least one conducting shell around at least a portion of said core.

6. The device of claim 5, wherein said core is spherical.

7. The device of claim 5, wherein said conducting shell is metal.

8. The device of claim 7, wherein said metal is gold.

9. The device of claim 7, wherein said metal is silver.

10. The device of claim 1, wherein said eyewear is a contact lens.

11. The device of claim 1, wherein said eyewear are goggles.

12. The device of claim 1, wherein said eyewear is a visor.

13. The device of claim 1, wherein said eyewear are glasses.

14. The device of claim 1, wherein said eyewear is an implant.

15. The device of claim 1, wherein said plasmon resonant particles are tunable.

16. The device of claim 15, wherein said plasmon resonant particles are tuned to reduce electromagnetic radiation energy passing through said eyewear.

17. The device of claim 15, wherein the plasmon resonant particles are tuned to permit at least 15% transmission of electromagnetic radiation energy having between 500 nm and 600 nm wavelengths to pass through said eyewear.

18. The device of claim 15, wherein the plasmon resonant particles are tuned to permit at least 30% transmission of electromagnetic radiation energy having between 500 nm and 600 nm wavelengths to pass through said eyewear.

19. Eyewear to reduce electromagnetic radiation entering the eye, said eyewear comprising:
a lens having a front surface and a back surface; and
plasmon resonant particles coated on at least one surface of said lens, wherein said plasmon resonant particles are characterized by a plasmon resonant peak in the electromagnetic frequency range between 670 nm and 1200 nm.

20. The eyewear of claim 19, wherein the plasmon resonant particles are nanoshells.

21. The eyewear of claim 19, wherein the plasmon resonant particles are nanorods.

22. The eyewear of claim 19, wherein the plasmon resonant particles are nanotubes.

23. The eyewear of claim 19, wherein the plasmon resonant particles comprise a non-conducting core and at least one conducting shell around at least a portion of said core.

24. The eyewear of claim 23, wherein said core is spherical.

25. The eyewear of claim 23, wherein said conducting shell is metal.

26. The eyewear of claim 25, wherein said metal is gold.

27. The eyewear of claim 25, wherein said metal is silver.

28. The eyewear of claim 23, wherein said core is characterized by a diameter which ranges from 80-500 nm.

29. The eyewear of claim 23, wherein said shell is characterized by a thickness which ranges from 7-35 nm.

30. The eyewear of claim 23, wherein said core is characterized by a diameter which is approximately 150 nm and said shell is characterized by a thickness which is approximately 17 nm.

31. The eyewear of claim 23, wherein said core is characterized by a diameter which is approximately 370 nm and said shell is characterized by a thickness which is approximately 15 nm.

32. The eyewear of claim 23, wherein said core is characterized by a diameter which is approximately 300 nm and said shell is characterized by a thickness which is approximately 17 nm.

33. The contact lens of claim 19, wherein said plasmon resonant particles are tunable.

34. The contact lens of claim 33, wherein said plasmon resonant particles are tuned to reduce electromagnetic radiation energy passing through said lens.

35. The contact lens of claim 34, wherein said reduction in electromagnetic radiation energy is between 670 nm and 1200 nm wavelengths.

36. The eyewear of claim 35, wherein said reduction in electromagnetic radiation energy between 670 nm and 1200 nm wavelengths is greater than 50%.

37. The eyewear of claim 35 wherein said reduction in electromagnetic radiation energy between 670 nm and 1200 nm wavelengths is greater than 90%.

38. The contact lens of claim 33, wherein the plasmon resonant particles are tuned to permit at least 15% transmission of electromagnetic radiation energy having between 500 nm and 600 nm wavelengths to pass through said eyewear.

39. The contact lens of claim 33, wherein the plasmon resonant particles are tuned to permit at least 30% transmission of electromagnetic radiation energy having between 500 nm and 600 nm wavelengths to pass through said eyewear.

40. The eyewear of claim 19, wherein said lens is a contact lens.

41. A contact lens comprising:
a lens having a front surface and a back surface; and
plasmon resonant particles coated on at least one surface of said lens, wherein said contact lens is characterized by an overall volume and said plasmon resonant particles comprise less than 1% of the overall volume.

42. The contact lens of claim 41, wherein said contact lens is characterized by an overall volume and said plasmon resonant particles comprise less than 15% of the overall volume.

43. A contact lens comprising:
a lens having a front surface and a back surface; and
plasmon resonant particles coated on at least one surface of said lens, wherein said plasmon resonant particles are characterized by an extinguishing curve which curve has a peak Plasmon resonance frequency portion and a trough portion that can be expressed as a ratio, wherein said ratio ranges from 2-7.

44. A contact lens comprising:
a lens; and
tunable nanoshells embedded in said lens,
wherein said contact lens is characterized by an overall volume, said nanoshells comprising a non-conducting silica core and a metal shell around at least a portion of said core, wherein said core is characterized by a diameter in the range of 80-500 nm and said shell is characterized by a thickness in the range of 7-35 nm and said nanoshells comprise less than 1% of the overall volume of said contact lens.

45. A method of manufacturing eyewear, said method comprising:
providing plasmon resonant particles tuned to reduce a desired wavelength in the electromagnetic energy spectrum;
dispersing said plasmon resonant particles in a polymer;
utilizing said polymer to form said eyewear, wherein said plasmon resonant particles are tuned to reduce electromagnetic radiation energy passing through said eyewear and wherein said reduction in electromagnetic radiation energy is between 670 nm and 1200 nm wavelengths.

46. The method of claim 45, further comprising the steps of utilizing said polymer to form a blank;
cutting a disk from said blank; and
lathing said disk to form said eyewear.

47. The method of claim 46, wherein said eyewear is a contact lens.

48. A method of manufacturing a contact lens, said method comprising:
providing nanoshells tuned to reduce a desired wavelength in the electromagnetic energy spectrum;
dispersing said nanoshells in 2-hydroxyethylmethacrylate (HEMA);
polymerizing said HEMA; and
utilizing said polymer to form a contact lens, wherein said plasmon resonant particles are tuned to reduce electromagnetic radiation energy passing through said contact lens and wherein said reduction in electromagnetic radiation energy is between 670 nm and 1200 nm wavelengths.

49. A method of manufacturing a contact lens, said method comprising:
providing nanoshells tuned to reduce a desired wavelength in the electromagnetic energy spectrum;
functionalizing said nanoshells with a molecule to provide stability during dispersion;
dispersing said nanoshells in a polymer; and
utilizing said polymer to form a contact lens, wherein said plasmon resonant particles are tuned to reduce electromagnetic radiation energy passing through said lens and wherein said reduction in electromagnetic radiation energy is between 670 nm and 1200 nm wavelengths.

50. The method of claim 49, wherein said molecule is polyvinylpyrrolidone (PVP).

51. The method of claim 49, wherein said molecule is polyvinylalcohol (PVA).

52. A device to reduce electromagnetic radiation entering the eye, comprising:
eyewear; and
plasmon resonant particles, integrated with said eyewear, wherein the plasmon resonant particles comprise a non-conducting core and at least one conducting shell around at least a portion of said core, wherein said core is characterized by a diameter which ranges from 80-500 nm.

53. A device to reduce electromagnetic radiation entering the eye, comprising:
eyewear; and
plasmon resonant particles, integrated with said eyewear, wherein the plasmon resonant particles comprise a non-conducting core and at least one conducting shell around at least a portion of said core, wherein said shell is characterized by a thickness which ranges from 7-35 nm.

54. A device to reduce electromagnetic radiation entering the eye, comprising:
eyewear; and
plasmon resonant particles, integrated with said eyewear, wherein the plasmon resonant particles comprise a non-conducting core and at least one conducting shell around at least a portion of said core, wherein said core is characterized by a diameter which is approximately 150 nm and said shell is characterized by a thickness which is approximately 17 nm.

55. A device to reduce electromagnetic radiation entering the eye, comprising:
eyewear; and
plasmon resonant particles, embedded in said eyewear, wherein said device is characterized by an overall volume and said plasmon resonant particles comprise less than 1% of the overall volume.

56. A device to reduce electromagnetic radiation entering the eye, comprising:
eyewear; and
plasmon resonant particles, embedded in said eyewear, wherein said plasmon resonant particles are tuned to reduce electromagnetic radiation energy passing through said and eyewear, wherein said reduction in electromagnetic radiation energy is between 670 nm and 1200 nm wavelengths.

57. The device of claim 56, wherein said reduction in electromagnetic radiation energy between 670 nm and 1200 nm wavelengths is greater than 50%.

58. The device of claim 56 wherein said reduction in electromagnetic radiation energy between 670 nm and 1200 nm wavelengths is greater than 90%.

59. A device to reduce electromagnetic radiation entering the eye, comprising:
eyewear; and
plasmon resonant particles, embedded in said eyewear, wherein said plasmon resonant particles are characterized by an extinguishing curve which curve has a peak Plasmon resonance frequency portion and a trough portion that can be expressed as a ratio, wherein said ratio ranges from 2-7.

60. Eyewear comprising:
a lens having a front surface and a back surface; and
plasmon resonant particles disposed between the front and back surface of said lens, wherein said plasmon resonant particles are tuned to reduce electromagnetic radiation energy passing through said lens and wherein said reduction in electromagnetic radiation energy is between 670 nm and 1200 nm wavelengths.

61. A method of manufacturing eyewear, said method comprising:
providing plasmon resonant particles tuned to extinguish a desired wavelength in the electromagnetic energy spectrum;
dispersing said plasmon resonant particles in a polymer;
utilizing said polymer to form said eyewear, wherein said plasmon resonant particles are tuned to extinguish at least 50% of the electromagnetic radiation energy between 670 nm and 1200 nm wavelengths passing through said eyewear.

62. A method of manufacturing eyewear, said method comprising:
providing plasmon resonant particles tuned to extinguish a desired wavelength in the electromagnetic energy spectrum;
dispersing said plasmon resonant particles in a polymer;
utilizing said polymer to form said eyewear, wherein said plasmon resonant particles are tuned to extinguish at least 90% of the electromagnetic radiation energy between 670 nm and 1200 nm wavelengths passing through said eyewear.

63. Eyewear to reduce electromagnetic radiation entering the eye, said eyewear comprising:
a lens having a front surface and a back surface; and
plasmon resonant particles integrated with said lens, wherein said plasmon resonant particles are tuned to reduce electromagnetic radiation energy passing through said lens and wherein said reduction in electromagnetic radiation energy is between 670 nm and 1200 nm wavelengths.

64. The eyewear of claim 63, wherein said lens is a contact lens.

65. The eyewear of claim 63, wherein said plasmon resonant particles are disposed on at least one surface of said lens.

66. The eyewear of claim 63, wherein said plasmon resonant particles are embedded in said lens.

* * * * *